(12) United States Patent
Rothman

(10) Patent No.: US 9,198,587 B2
(45) Date of Patent: Dec. 1, 2015

(54) METHOD AND DEVICE FOR MULTIMODAL NEUROLOGICAL EVALUATION

(71) Applicant: BrainScope Company, Inc., Bethesda, MD (US)

(72) Inventor: Neil S. Rothman, Baltimore, MD (US)

(73) Assignee: BrainScope Company, Inc., Bethesda, MD (US)

( * ) Notice: Subject to any disclaimer, the term of this patent is extended or adjusted under 35 U.S.C. 154(b) by 0 days.

(21) Appl. No.: 14/322,355

(22) Filed: Jul. 2, 2014

(65) Prior Publication Data

US 2014/0316221 A1     Oct. 23, 2014

Related U.S. Application Data

(63) Continuation of application No. 13/352,618, filed on Jan. 18, 2012, now Pat. No. 8,792,974.

(51) Int. Cl.
| | |
|---|---|
| *A61B 5/04* | (2006.01) |
| *A61B 5/00* | (2006.01) |
| *A61B 5/0476* | (2006.01) |
| *A61B 5/0402* | (2006.01) |
| *A61B 5/0484* | (2006.01) |
| *G06F 19/00* | (2011.01) |

(52) U.S. Cl.
CPC ............ *A61B 5/04012* (2013.01); *A61B 5/0022* (2013.01); *A61B 5/0402* (2013.01); *A61B 5/0476* (2013.01); *A61B 5/04842* (2013.01); *A61B 5/6803* (2013.01); *A61B 5/7264* (2013.01); *A61B 5/7475* (2013.01); *G06F 19/345* (2013.01)

(58) Field of Classification Search
CPC .. A61B 5/7264; A61B 5/0205; A61B 5/0476; A61B 5/7267; G06N 99/005; G06N 3/02; G06N 3/12; G06N 3/126
USPC .......................... 600/544, 545; 382/159, 160
See application file for complete search history.

(56) References Cited

U.S. PATENT DOCUMENTS

| | | |
|---|---|---|
| 2003/0176806 A1 | 9/2003 | Pineda et al. |
| 2003/0225340 A1 | 12/2003 | Collura |

(Continued)

FOREIGN PATENT DOCUMENTS

| | | |
|---|---|---|
| CN | 101583308 A | 11/2009 |
| WO | WO 00/10455 A1 | 3/2000 |
| WO | WO 2008/148894 A1 | 12/2008 |
| WO | WO 2011/019889 A1 | 2/2011 |
| WO | WO 2011/115956 A1 | 9/2011 |
| WO | WO 2014/040175 A1 | 3/2014 |

OTHER PUBLICATIONS

International Search Report and Written Opinion corresponding to International Application No. PCT/US2013/021387 dated Apr. 3, 2013, 12 pages.

(Continued)

*Primary Examiner* — Etsub Berhanu
(74) *Attorney, Agent, or Firm* — Finnegan, Henderson, Farabow, Garrett & Dunner, LLP

(57) ABSTRACT

A method of building classifiers for multimodal neurological assessment is described. The method comprises the steps of extracting quantitative features from a plurality of physiological and neurocognitive assessments, and selecting a subset of features from the extracted pool of features to construct multimodal classifiers. A device for performing point-of-care multimodal neurological assessment is also described.

18 Claims, 3 Drawing Sheets

(56) References Cited

U.S. PATENT DOCUMENTS

| | | |
|---|---|---|
| 2005/0209785 A1 | 9/2005 | Wells et al. |
| 2007/0032737 A1 | 2/2007 | Causevic et al. |
| 2007/0191691 A1 | 8/2007 | Polanco |
| 2008/0208073 A1 | 8/2008 | Causevic |
| 2008/0243021 A1 | 10/2008 | Causevic et al. |
| 2009/0264785 A1 | 10/2009 | Causevic et al. |
| 2010/0191139 A1 | 7/2010 | Jacquin et al. |
| 2010/0324443 A1 | 12/2010 | Ashton-Miller et al. |
| 2011/0038515 A1 | 2/2011 | Jacquin et al. |
| 2011/0257267 A1 | 10/2011 | Hadley et al. |
| 2013/0184603 A1 | 7/2013 | Rothman |
| 2014/0081090 A1 | 3/2014 | Picard et al. |
| 2014/0107494 A1 | 4/2014 | Kato et al. |

OTHER PUBLICATIONS

Andrzej at al. "Multimodal Classification: Case Studies," Transactions on Rough Sets V, LNCS 4100 (2006) 224-239.

Quinlan, J.R. (1987). "Generating Production Rules From Decision Trees." Paper presented at the Tenth International Joint Conference on Artificial Intelligence, Milan, Aug. 23-28, (pp. 304-307). Netherlands: Morgan Kaufmann.

Wang, H et al., (2006). "Density maximization classification in the lattice machine," Paper presented at the Third International IEEE Conference on Intelligent Systems, London, Sep. 4-6, (pp. 12-16). New York: IEEE Press.

International Search Report and Written Opinion for International Application No. PCT/US2015/032374 dated Aug. 28, 2015 (13 pages).

METHOD AND DEVICE FOR MULTIMODAL NEUROLOGICAL EVALUATION

This application is a continuation of application Ser. No. 13/352,618, filed Jan. 18, 2012, which is incorporated herein by reference in its entirety.

The present disclosure relates to the field of neurological assessment, and specifically, to the development of a method and device for combining the results from multiple assessment technologies to provide a multi-dimensional evaluation of a subject's neurological condition.

Currently, objective assessment of brain function is limited to evaluation of a subject's brain electrical activity data collected through EEG (electroencephalography) recording. At a basic level, the brain electrical signals serve as a signature for both normal and abnormal brain function, and an abnormal brain wave pattern can be a strong indication of certain brain pathologies.

Objective assessment of brain electrical signals may be performed using a classifier that provides a mathematical function for mapping (or classifying) a vector of quantitative features extracted from the recorded EEG data into one or more predefined categories. Classifiers are built by forming a training dataset, where each subject is assigned a "label," namely a neurological class based on information provided by doctors and obtained with the help of state-of-the-art diagnostic systems, such as CT scan, MRI, etc. For each subject in the dataset, a large set of quantitative signal attributes or features (computed from the EEG) is also available. The process of building a classifier from a training dataset involves the selection of a subset of features (from the set of all quantitative features), along with the construction of a mathematical function which uses these features as input and which produces as its output an assignment of the subject's data to a specific class. After a classifier is built, it may be used to classify unlabeled data records as belonging to one or the other potential neurological classes. Classification accuracy is then reported using a testing dataset which may or may not overlap with the training set, but for which a priori classification data is also available. The accuracy of the classifier is dependent upon the selection of features that comprise part of the specification of the classifier. Selection of features that contribute most to the classification task ensures the best classification performance.

Although brain electrical activity data provides a valuable means for analyzing brain function, the presence or severity of certain heterogeneous types of brain injury or dysfunction, for example, traumatic brain injury (TBI), can be assessed more objectively by combining the results from a plurality of diagnostic tests. Accordingly, the present disclosure provides a method of expanding the classifier building process to integrate features or outputs from multiple assessment technologies into the feature selection process. The inclusion of features from multiple assessment technologies holds the promise of improving classification performance beyond that achieved with features derived only from brain electrical signals.

The present disclosure describes a method of building a classification system for real-time evaluation of a subject's neurological state, wherein the classification system combines the results/outputs from multiple assessment technologies to perform multimodal assessment of the subject's condition. A first aspect of the present disclosure comprises a method of building a classifier for multimodal assessment of a subject's neurological condition. The method comprises the step of providing a signal processing device operatively connected to a memory device which stores results of different assessments performed on a plurality of individuals in the presence or absence of brain abnormalities. The signal processing device comprises a processor configured to obtain results of two or more different assessments from the memory device, extract quantitative features from the results of the two or more assessment, store the extracted features in a pool of selectable features, select a subset of features from the pool of selectable features to construct the classifier, and determine classification accuracy of the classifier by using it to classify data records having a priori classification information.

A second aspect of the present disclosure is another method of building a classifier for classification of individual data into one of two or more categories of neurological condition. The method comprises the steps of providing a processor configured to build a classifier, and providing a memory device operatively coupled to the processor, wherein the memory device stores a population reference database comprising a pool of quantitative features extracted from the results of two or more physiological and neurocognitive assessments performed on a plurality of individuals in the presence or absence of brain abnormalities. The processor is configured to select a plurality of features from brain electrical activity data and one or more other assessments performed on the plurality of individuals in the population reference database, constructing a classifier using the selected quantitative features, and evaluating performance of the classifier using pre-labeled data records that are assigned a priori to one of the two categories.

A yet another aspect of the disclosure is a device for performing multimodal assessment of a subject's neurological condition. The device includes a headset comprising one or more neurological electrodes configured to record the subject's brain electrical activity, an input device configured to acquire results of one or more physiological and neurocognitive assessments performed on the subject, and a base unit operatively coupled to the headset and the input device. The base unit comprises a processor configured to perform the steps of extracting quantitative features from the brain electrical activity data and the other physiological and neurocognitive assessments performed on the subject, and further applying a multimodal classifier to perform classification of the subject's neurological condition into one of two or more categories.

It is to be understood that both the foregoing general description and the following detailed description are exemplary and explanatory only and are not restrictive of the invention, as claimed. The terms "EEG signal" and "brain electrical signal" are used interchangeably in this application to mean signals acquired from the brain using neurological electrodes.

The accompanying drawings, which are incorporated in and constitute a part of this specification, illustrate embodiments of the invention and together with the description, serve to explain the principles of the various aspects of the invention.

DESCRIPTION OF ILLUSTRATIVE EMBODIMENTS

Reference will now be made in detail to certain embodiments consistent with the present disclosure, examples of which are illustrated in the accompanying drawings. Wherever possible, the same reference numbers will be used throughout the drawings to refer to the same or like parts.

Multimodal Classifier Building Method

The present disclosure describes a method for building a classifier for mapping multi-modal assessment data into one or more predefined neurological classes or categories. In an exemplary embodiment, the multiple assessment technologies include various neurophysiological assessments tools, for example, EEG recording, infrared testing to look for blood in the head, clinical testing of biomarkers that indicate brain injury, reaction time testing, eye movement tracking, etc. In another exemplary embodiment, the multiple assessment technologies additionally include neurocognitive assessment (such as, Standardized Assessment of Concussion (SAC), Automated Neurophysiological Assessment Metrics (ANAM), ImPACT, etc.). In yet another exemplary embodiment, the multiple assessment technologies further include other physiological testing, such as, electrocardiography (ECG or EKG), heart rate variability testing, galvanic skin response testing, etc. The results provided by the multiple assessment technologies are integrated to provide the best classification or assessment performance.

Figure 1:
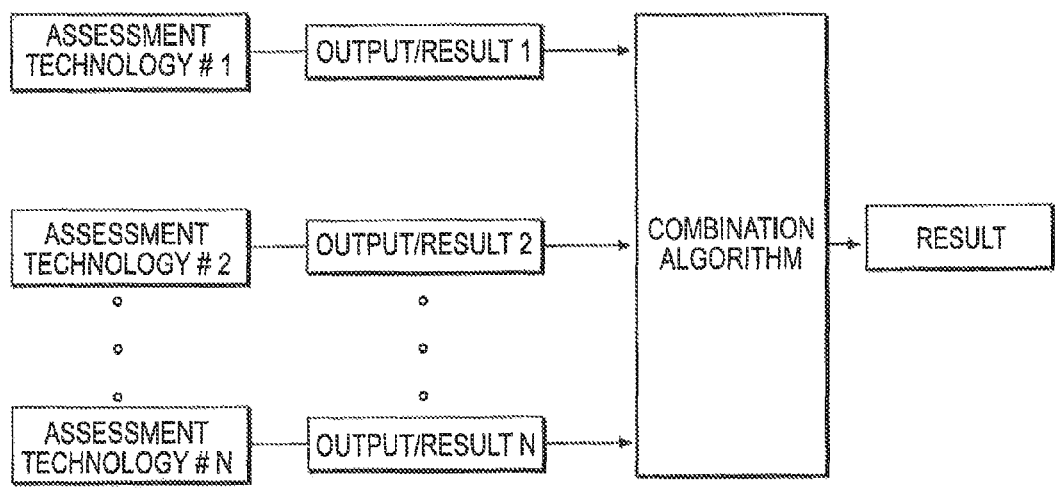
FIG. 1 illustrates a prior art approach to combining results of multiple assessments.

In a conventional approach to combining results of multiple assessments, the outputs of two or more technologies are combined using an algorithm, such as, tree logic, voting methods, or weighted combinations, etc., to provide a combined result, as illustrated in FIG. 1. This is analogous to a physician using the results of multiple tests to diagnose a patient's condition. The result or output from each assessment is provided as an input to the combination algorithm, which is applied to each subject to make an overall classification or assessment of the subject's neurological state. In contrast, the present disclosure describes a method that enables inclusion of results/outputs from multiple technologies as selectable features in the algorithm development process. The integration of multimodal assessment data in the algorithm development process offers a distinct advantage in multi-class classification applications where the results of certain assessment technologies are not relevant to all of the classes. In such cases, the inclusion of extraneous assessments could potentially distort the overall classification result. The method described in the present disclosure overcomes this disadvantage by enabling the training of the classification algorithm to identify results/features (from all available assessment results) that contribute the most to each classification task.

Figure 2:
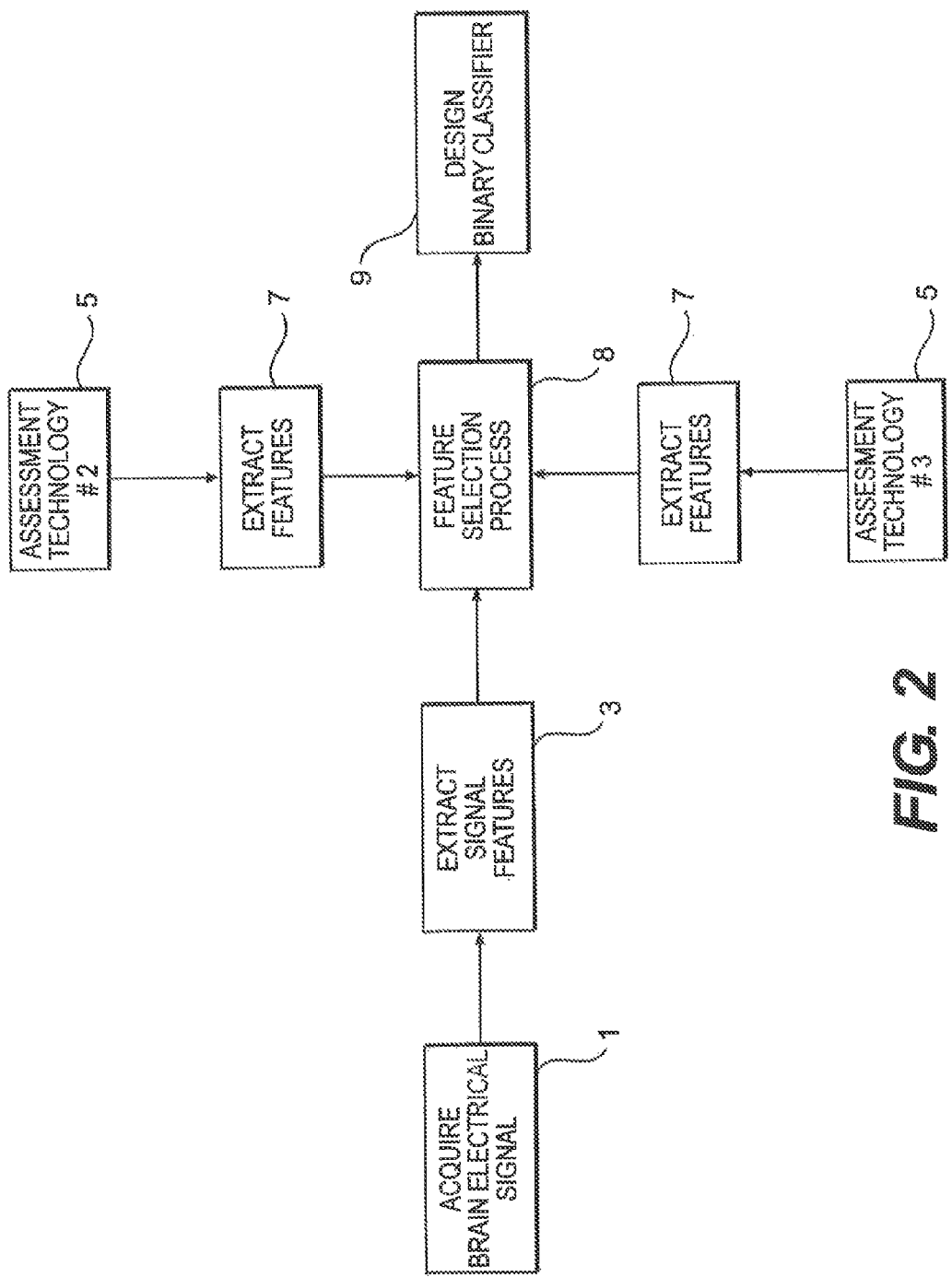
FIG. 2 is a flowchart of a multimodal classifier building process, in accordance with an exemplary embodiment of the present disclosure.

An exemplary classifier building methodology is illustrated in FIG. 2. The classifier building algorithm, as illustrated in FIG. 2, is executed by a signal processing device comprising a processor. An initial step in the classifier building process is the collection of raw brain electrical signals (step 201). In an exemplary embodiment, a subject's electrical brain activity is recorded using a varying number of non-invasive neurological electrodes located at standardized positions on the scalp and forehead and ear-lobes. In one exemplary embodiment, a subject's brain electrical activity is recorded using an electrode array comprising at least one neurological electrode to be attached to a patient's head to acquire the brain electrical signals. The electrodes are configured for sensing both spontaneous brain activity as well as evoked potentials generated in response to applied stimuli (e.g. auditory, visual, tactile stimuli, etc.). In exemplary embodiments, the signal processor running the classifier building algorithm is configured to implement an artifact detection algorithm to identify data that is contaminated by non-brain-generated artifacts, such as eye movements, electromyographic activity (EMG) produced by muscle tension, spike (impulse), external noise, etc., as well as unusual electrical activity of the brain not part of the estimation of stationary background state. An exemplary artifact detection method is described in U.S. application Ser. No. 13/284,184, which is incorporated herein by reference in its entirety.

The artifact-free data epochs are then processed to extract quantitative signal features (step 3), in an exemplary embodiment, the processor is configured to perform a linear feature extraction algorithm based on Fast Fourier Transform (FFT) and power spectral analysis, according to a method disclosed in commonly-assigned U.S. Pat. Nos. 7,720,530 and 7,904,144, which are incorporated herein by reference in their entirety. In another embodiment, the processor is configured to perform feature extraction based on wavelet transforms, such as Discrete Wavelet Transform (DWT) or Complex Wavelet Transforms (CWT). In yet another embodiment, the processor is configured to perform feature extraction using non-linear signal transform methods, such as wavelet packet transform, according to a method disclosed in commonly-assigned U.S. patent application Ser. No. 12/361,174, which is incorporated herein by reference in its entirety. The features extracted by this method are referred to as Local Discriminant Basis (LDB) features. In another embodiment, diffusion geometric analysis is used to extract non-linear features according to a method disclosed in commonly-assigned U.S. patent application Ser. No. 12/105,439, which is incorporated herein by reference in its entirety. In yet other embodiments, entropy, fractal dimension, and mutual information-based features are also calculated.

In exemplary embodiments, the computed measures per epoch are combined into a single measure of EEG signal per channel and transformed for Gaussianity. Once a Gaussian distribution has been demonstrated and age regression applied, statistical Z transformation is performed to produce Z-scores. The Z-transform is used to describe the deviations from age expected normal values:

$$Z = \frac{\text{Subject Value} - \text{Norm for Age}}{\text{Standard Deviation for Age}}$$

The Z-scores are calculated for each feature and for each electrode, pair of electrodes, or pair of a pair of electrodes, using a database of response signals from a large population of subjects believed to be normal, or to have other pre-diagnosed conditions. In particular, each extracted feature is converted to a Z-transformed score, which characterizes the probability that the extracted feature observed in the subject will conform to a normal value. The age-regressed and Z-transformed signal features are stored in a population reference database. The database is stored in a memory device that is operationally coupled to the signal processor executing the classifier building algorithm.

Referring again to FIG. 2, the next step in the algorithm development process is the collection of results from other assessment modalities (step 5) and extraction of quantitative features from the other assessment results (step 7). For example, in one embodiment, the multimodal assessments include reaction time testing. One or more quantitative features are calculated from the results of the reaction time testing. Reaction time test looks at the time it takes a subject to respond to an applied stimuli (visual, auditory, etc.) and compares it to a normative value. Quantitative features are calculated from the results of multiple trials (e.g., the mean and standard deviation of multiple test results). In exemplary embodiments, the features of interest are z-scored and stored in the population reference database for use in the algorithm development process. Similarly, quantitative features are calculated from the output of other assessment technologies (e.g., EKG, galvanic skin reaction testing, etc.). The features are transformed into z-scores and stored in the population reference database.

In an exemplary embodiment, neurocognitive assessment is performed alongside the physiological evaluations. In some embodiments, the neurocognitive assessment is performed using standardized questionnaires for testing the presence or severity of neurocognitive impairment following an injury, such as, the Standardized Assessment of Concussion (SAC), Automated Neurophysiological Assessment Metrics (ANAM), ImPACT, etc. In other embodiments, the neurocognitive assessment is performed using a dynamic questionnaire created from expert neuropsychological assessment practices. The questionnaire is designed to dynamically adapt to responses given by a subject, i.e., each subject may not be asked exactly the same set of questions. Data from the neurocognitive assessment is processed to extract quantitative features, for example, reaction time metrics, severity ranking of symptoms, normalized combinations of symptoms or clinical manifestations, etc., which are entered into the pool of selectable features in the reference database. In case of the dynamic questionnaire, the features that are entered into the database are based on the overall quantitative output from the questionnaire and not based on any specific assessment metrics.

Once features are extracted from the various assessment technologies and stored in the reference database, the next step in the algorithm development process in the selection of features that provide the best classification performance (step 8). The weights and constants that define a classification function (such as, Linear Discriminant Function, Quadratic Discriminant Function, etc.) are derived from a set of quantitative features in the population reference database. Thus, the design or construction of a classification function targeting any classification task (e.g. "Normal" vs. "Abnormal" brain function) requires selection of a set of features from a large available pool of features in the population reference database. The selection of the "best" features results in the "best" classification performance, characterized by, for example, the highest sensitivity/specificity and lowest classification error rates. In order to make the feature selection process more efficient and to ensure higher classification performance, the available pool of features from the multiple assessment modalities must be transformed or reduced to a computationally manageable and neurophysiologically relevant pool of features from which a subset of features for a particular classification task may be selected during classifier construction.

Accordingly, in some exemplary embodiments, the pool of available features in the population reference database is reduced to a smaller set of features that contribute directly to a specific classification task. In an exemplary embodiment, a reduced pool of features is created using an "informed data reduction" technique, which relies on the specific downstream application of the classifier, neurophysiology principles and heuristic rules. In exemplary embodiments, the "informed data reduction" method includes several different criteria to facilitate the inclusion of features that most effectively provide separation among the classes. The "informed data reduction" method is described in U.S. application Ser. No. 13/284,184, which is incorporated herein by reference.

Once all the data reduction criteria are applied, the remaining reduced pool of features is utilized to design a classifier (step 9). In one exemplary embodiment, the classifier is a binary classifier used to classify individual data records as belonging to one of two classes. In another exemplary embodiment, the classifier is a multiclass classifier used to classify data records into more than two classes. In yet another exemplary embodiment, a series of binary classifiers that use either linear or non-linear discriminant functions are used to classify individuals into multiple categories. In some embodiments, x-1 discriminant functions are used to separate individual subjects into x classification categories. In an exemplary embodiment, three binary classifiers are designed and implemented for classifying patients Into one of four categories related to the extent of brain dysfunction resulting from a traumatic brain injury (TBI), as described in U.S. application Ser. No. 12/857,504, which is incorporated herein by reference.

The construction of a classifier is now described with reference to a binary classifier. In exemplary embodiments, a binary classifier is designed by selecting a specific set of features for each discriminant function based on performance. The search for the "best" features for a binary classification task is performed using a fully-automated system (hereinafter "classifier builder"), implemented as a computer program, the output of which is a Discriminant Function classifier. In exemplary embodiments, identification of the "best" features for a particular classification task is performed by computing multiple classifiers using different combination of features, and evaluating each possible classifier using an "objective function" that is directly related to classification performance. In an exemplary embodiment, the objective function (figure of merit) used by a feature selection algorithm is the area under the Receiver Operating Characteristics (ROC) curve of a Discriminant Function, which is usually referred to as "Area Under the Curve" (AUC). For a given discriminant-based binary classifier, the ROC curve indicates the sensitivity and specificity that can be expected from the classifier at different values of the classification threshold T. Once a critical value (or threshold) T is selected, the output of the test becomes binary, and sensitivity and specificity for that particular threshold can be calculated. The ROC is the curve through the set of points: {(1-specificity(T), sensitivity(T))}, which is obtained by varying the value of the threshold T in fixed increments between 0 and 100. After the ROC curve is obtained, the area under the ROC curve (AUC) is calculated. AUC is a single number between 0 and 1, which reflects, jointly, the sensitivity and specificity of a binary classifier. Thus, AUC provides a quantitative global measure of achievable classifier performance.

In one exemplary embodiment, the search for the "best" features for a classification task is performed using a feature selection algorithm that is referred to herein as "Simple Feature Picker" (SFP) algorithm. The SFP algorithm selects a first feature by evaluating all features in the database or the reduced pool of features, and selects the feature that provides the best classifier performance. Subsequent features are selected to give the best incremental improvement in classifier performance. In another exemplary embodiment, the SFP algorithm adds multiple features to the classifier at each iteration, calculates AUC of the resulting classifier at each iteration step, and selects the features that provide that greatest improvement in AUC.

In another exemplary embodiment, feature selection is performed using one or more evolutionary algorithms, for example, a Genetic Algorithm (GA), as described in commonly-owned U.S. application Ser. No. 12/541,272 which is incorporated herein by reference in its entirety. In yet another exemplary embodiment, the search for candidate features is performed using an optimization method, for example, Random Mutation Hill-Climbing (RMHC) method, or Modified Random Mutation Hill Climbing (mRMHC), which can be used in a stand-alone fashion or can be combined with the GA algorithm or SFP algorithm (for example, as a final "local search" to replace one feature by another to improve the final feature subset), as further described in the U.S. application Ser. No. 12/541,272 incorporated herein.

After a classifier is built, classification accuracy is evaluated using a testing dataset comprising pre-labeled data records which are assigned a priori to one of the classification categories. In some embodiments, the testing dataset is separate from the training set. In some other exemplary embodiments, all available data is used for both training and testing of the classifier. In such embodiments, performance of the classifier is evaluated using 10-fold and/or leave-one-out (LOO) cross-validation methods, as described in U.S. application Ser. Nos. 12/857,504, and 13/284,184, which are incorporated herein by reference. After a classifier is built and tested for accuracy, it may be used to classify unlabeled data records (i.e., unknown subjects) as belonging to a particular class.

Portable Device for Field Applications

Figure 3:
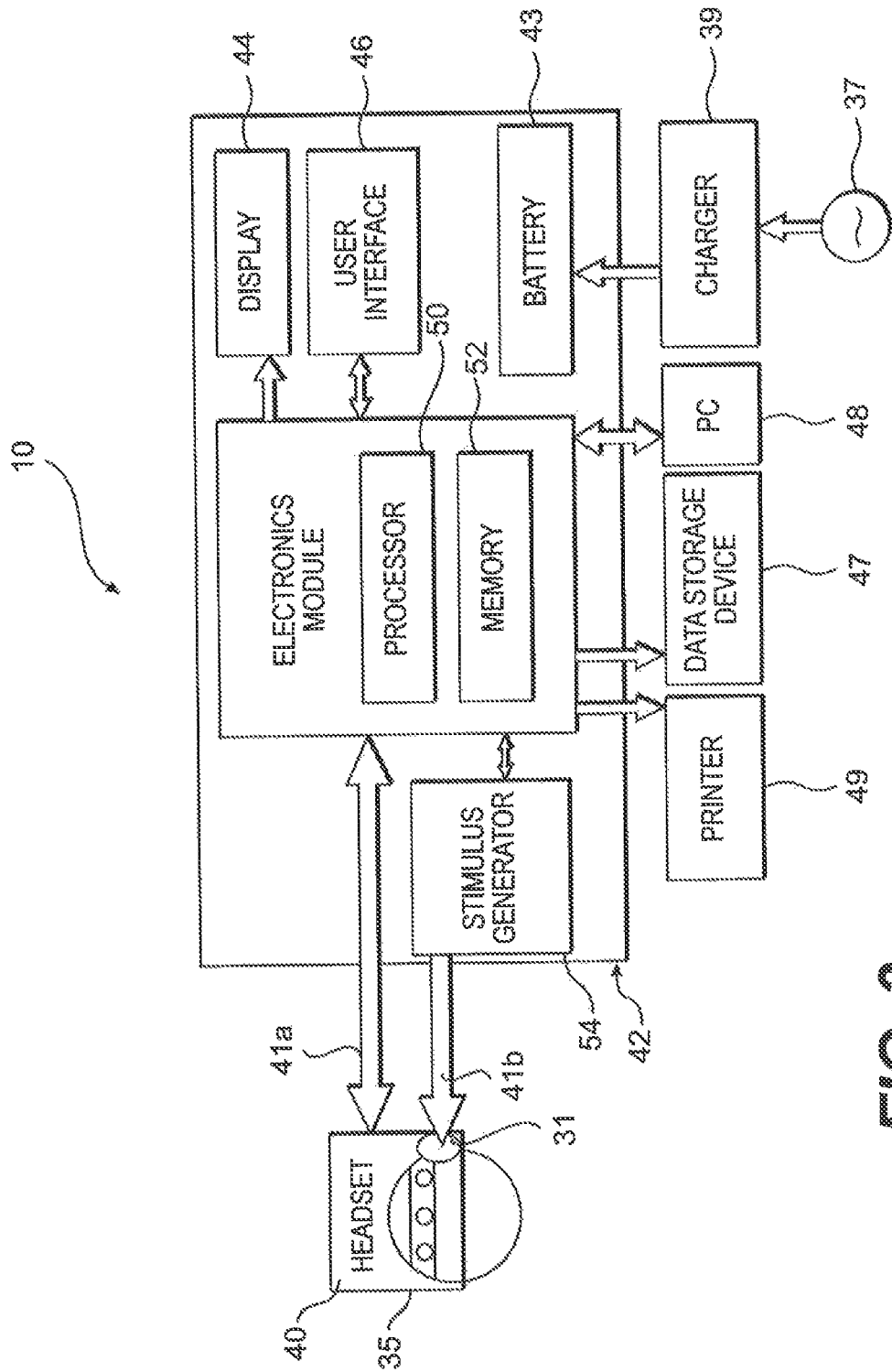
FIG. 3 illustrates a multimodal neuroassessment apparatus, in accordance with exemplary embodiments of the present disclosure.

Another aspect of the present disclosure is an apparatus for performing multimodal neurological triage on a subject, FIG. 3 illustrates a multimodal neuro-assessment apparatus 10, in accordance with exemplary embodiments of the present disclosure. In an exemplary embodiment, the neuro-assessment apparatus 10 is implemented as a portable device for point-of-care applications. The apparatus consists of a headset 40 which may be coupled to a base unit 42, which can be handheld. Headset 40 may include a plurality of electrodes 35 to be attached to a patient's head to acquire brain electrical signals. The electrodes are configured for sensing both spontaneous brain activity as well as evoked potentials generated in response to applied stimuli, such as audio, tactile, or electrical stimuli. In an exemplary embodiment, recording is done using five (active) channels and three reference channels. The electrode array consists of anterior (frontal) electrodes: Fp1, Fp2, F7, F8, AFz (also referred to as Fz') and Fpz (reference electrode) to be attached to a subject's forehead, and electrodes A1 and A2 to be placed on the front or back side of the ear lobes, or on the mastoids, in accordance with the International 10/20 electrode placement system (with the exception of AFz). Other electrode configurations may be utilized as and when required, as would be understood by those of ordinary skill in the art. The use of a limited number of electrodes enable rapid and repeatable placement of the electrodes on a subject, which in turn facilitates efficient, and more accurate, patient monitoring. Further, in one embodiment, the electrodes may be positioned on a low-cost, disposable platform, which can serve as a "one-size-fits-all" sensor. For example, electrodes 35 may be positioned on a head gear that is configured for easy and/or rapid placement on a patient, as further set forth in commonly assigned U.S. patent application Ser. No. 12/059,014, which is incorporated herein by reference in its entirety. Other electrode configurations may be utilized as and when required, as would be understood by those of ordinary skill in the art.

In an exemplary embodiment, the neuro-assessment apparatus 10 utilizes the advantages of auditory evoked potential (AEP) signals to map specific auditory, neurological and psychiatric dysfunctions. In such an embodiment, the headset 40 includes reusable earphone 31 to provide auditory stimuli clicks in either ear. In some embodiments, the auditory evoked potential signal used is auditory brainstem response (ABR). In such embodiments, the auditory stimuli may be delivered at 100 dB Peak-to-Peak Equivalent Sound Pressure Level and at a frequency (rate) of 27 Hz (27 clicks per second) to evoke electrical signals from the brainstem in response to the applied auditory stimuli. Other auditory stimuli may also be used, to evoke mid-latency (20-80 milliseconds) or late auditory responses (>80 milliseconds), including the P300. In another embodiment, headset 40 may include an additional ear phone to deliver white noise in the other ear.

In another exemplary embodiment, the neuro-assessment device 10 utilizes visual evoked potentials (VEP) to evaluate the extent of brain injury or dysfunction. For example, in some embodiments, VEP is used to evaluate post-trauma vision syndrome (PTVS) in patients with traumatic brain injuries (TBI). In one exemplary embodiment, monocular and binocular VEPs are recorded under various stimulus conditions provided by the base unit 42 through display 44. In another exemplary embodiment, headset 40 includes a pair of goggles to provide visual stimuli to patients. In one such embodiment, the goggles are mounted with light emitting diodes (LEDs) to provide flash stimuli to elicit VEPs. In another embodiment, the goggles are mounted with a video monitor to provide pattern stimuli to patients.

In addition to acquiring brain electrical signals, neuro-assessment apparatus 10 is designed to collect the output from other assessment technologies. In one embodiment, the results from other assessment modalities are manually entered by the user. In another embodiment, the results are acquired electronically via wireless or other communication methods. In yet another embodiment, apparatus 10 comprises an accessory device for administering a test and acquiring results. For example, in some embodiments, reaction time testing is performed using an input device, such as, a graphical user interface, which is independent of user interface 46. The independent input device is used to minimize latency errors, and thereby improve reaction time measurements.

Referring back to FIG. 3, display 44 in the base unit 42 comprises a LCD screen, and can further have a user interface 46, which can be a touch screen user interface or a traditional keyboard-type interface. Communication link 41 can act as a multi-channel input/output interface for the headset 40 and the handheld device 42, to facilitate bidirectional communication of signals to and from the processor 50, such that, for example, a command from the user entered through the user interface 46 can start the signal acquisition process of the headset 40. Communication link 41 may include a permanently attached or detachable cable or wire, or may include a wireless transceiver, capable of wirelessly transmitting signals and receiving signals from the headset, or from an external device storing captured signals. In exemplary embodiments, communication link 41 includes two reusable patient interface cables which are designed to plug into the base unit 42 and provide direct communication between the headset 40 and base unit 42. The first cable is an electrical signal cable 41a, which is equipped with standard snap connectors to attach to the disposable electrodes placed on the patient's scalp. The second cable is the AEP stimulus cable 41b which provides connection to the earphone 31 for auditory stimulus delivery. In some embodiments, the headset 40 includes analog amplification channels connected to the electrodes, and an analog-to-digital converter (ADC) to digitize the acquired brain electrical signals prior to receipt by the base unit 42.

In an exemplary embodiment, the brain electrical activity data and the results of the other physiological and neurocognitive assessment technologies are processed by signal processor 50 in the hand-held base unit 42. Processor 50 is configured to perform real-time evaluation of a subject's neurological state using instructions stored in memory device 52. In exemplary embodiments, processor 50 is configured to apply one or more multimodal classifiers to combine the results/outputs from a plurality of assessment technologies and provide a multi-dimensional evaluation of the subject's condition. In one such embodiment, processor 50 is configured to extract quantitative features from the results of the physiological and neurocognitive assessments, and apply one or more discriminant functions to classify an unknown subject as belonging to one of two or more neurological categories.

In illustrative embodiments, memory device 52 contains interactive instructions for using and operating the device to be displayed on screen 44. The instructions may comprise an interactive feature-rich presentation including a multimedia recording providing audio/video instructions for operating the device, or alternatively simple text, displayed on the screen, illustrating step-by-step instructions for operating and using the device. The inclusion of interactive instructions with the device eliminates the need for extensive user training, allowing for deployment and uses by persons other than medical professional. In some embodiments, the memory 52 may also contain the population reference database. In other embodiments, the reference database may be accessed from a remote storage device via a wireless or a wired connection. Further, in some exemplary embodiments, memory 52 includes a dynamic software designed to lead a medical personnel with minimal training through a step-by-step assessment of a subject. The software is designed to present assessment questions to the user based on responses provided by the subject to prior questions. The questions are designed to guide the user through the various available assessment tools.

The classification result obtained from processor 50 is displayed on the display screen 44, or saved in external memory or data storage device 47, or displayed on a PC 48 connected to the base unit 42. In one embodiment, base unit 42 contains a wireless transceiver to transmit the results wirelessly to a remote network or PC 48, or the external memory 47 to store the results. In some embodiments, the neuro-assessment apparatus 10 can also transmit data to another mobile or stationary device to facilitate more complex data processing or analysis. For example, the neuro-assessment device, operating in conjunction with PC 48, can send data to be further processed by the computer. In another embodiment, the results can be transmitted wirelessly or via a cable to a printer 49 that prints the results. Base unit 42 can also contain an internal rechargeable battery 43 that can be charged during or in between uses by battery charger 39 connected to an AC outlet 37. The battery can also be charged wirelessly through electromagnetic coupling by methods known in the prior art. In some embodiments, the base unit 42 further includes a stimulus generator 54 for applying stimuli to the subject for AEP measurement, or for reaction time measurement. In some embodiments, the stimulus generator is included in the headset 40.

In another exemplary embodiment, user interface 46 receives and displays usage setting information, such as the name, age and/or other statistics pertaining to the patient. In some embodiments, the user interface 46 comprises a touchscreen for entering the user input. A virtual keypad may be provided on the touchscreen interface for input of patient record.

The neuro-assessment apparatus 10 is designed for near-patient testing in emergency rooms, ambulatory setting, and other field applications. The neuro-assessment device is intended to be used in conjunction with CT scan, MRI or other imaging studies to provide complementary or corroborative information about a patient's neurological condition. The key objective of point-of-care neuro-assessment is to provide fast results indicating the severity of a patient's neurological condition, so that appropriate treatment can be quickly provided, leading to an improved overall clinical outcome. For example, neuro-assessment device 10 may be used by an EMT, ER nurse, or any other medical professional during an initial patient processing in the ER or ambulatory setting, which will assist in identifying the patients with emergency neurological conditions. It will also help ER physicians in corroborating an immediate course of action, prioritizing patients for imaging, or determining if immediate referral to a neurologist or neurosurgeon is required. This in turn will also enable ER personnel to optimize the utilization of resources (e.g., physicians' time, use of imaging tests, neuro consults, etc.) in order to provide safe and immediate care to all patients.

In addition, neuro-assessment device 10 is designed to be field-portable, that is, it can be used in locations far removed from a full-service clinic—for example, in remote battlefield situations distant from military healthcare systems, during sporting events for identifying if an injured athlete should be transported for emergency treatment, at a scene of mass casualty in order to identify patients who need critical attention and immediate transport to the hospital, or at any other remote location where there is limited access to well-trained medical technicians.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A device for multimodal assessment of a subject's neurological condition, the device comprising:
   a headset comprising one or more neurological electrodes configured to record the subject's brain electrical signals;
   a base unit operatively coupled to the headset and configured to acquire results of one or more physiological assessments and/or neurocognitive assessments performed on the subject, the base unit further comprising a processor configured to perform the steps of:
   extracting quantitative features from the brain electrical signals;
   extracting quantitative features from the results of the one or more physiological assessments and/or neurocognitive assessments performed on the subject; and
   applying a multimodal classifier to provide a multi-dimensional evaluation of the subject's neurological condition, wherein the multimodal classifier is configured to combine the extracted quantitative features from the brain electrical signals and extracted quantitative features from the results of the one or more physiological assessments and/or neurocognitive assessments, and further wherein the multimodal classifier is pre-developed and pre-trained using selectable features from a training dataset comprising brain electrical activity data and one or more physiological assessments and/or neurocognitive assessments data obtained from a plurality of individuals in the presence or absence of brain abnormalities.

2. The device of claim 1, wherein the processor is configured to perform automatic identification and removal of artifacts from the brain electrical signals.

3. The device of claim 1, wherein the base unit is operatively coupled to an input device, and wherein the input device is configured to acquire the results of the one or more physiological assessments and/or neurocognitive assessments.

4. The device of claim 1, wherein the base unit is configured to wirelessly receive the results of the one or more physiological assessments and/or neurocognitive assessments.

5. The device of claim 1, further comprising a memory device for storing interactive instructions for using and operating the device.

6. The device of claim 5, wherein the memory device stores a dynamic questionnaire that provides step-by-step instructions for performing the multimodal assessment.

7. The device of claim 1, further comprising a touch-screen interface to enter user input.

8. The device of claim 1, wherein the base unit is a handheld device.

9. The device of claims 1, wherein the one or more physiological and/or neurocognitive assessments comprise recording of electrocardiographic signals.

10. The device of claim 1, wherein the multimodal classifier comprises one or more discriminant functions.

11. The device of claim 1, wherein the multimodal classifier is a binary classifier.

12. The device of claim 1, wherein the multimodal classifier is a multi-class classifier.

13. The device of claim 1, further comprising a monitor for providing visual stimuli to the subject to elicit visual evoked potentials.

14. The device of claim 1, further comprising a pair of goggles for providing visual stimuli to the subject to elicit visual evoked potentials.

15. The device of claim 1, further comprising one or more earphones to provide auditory stimuli to the subject to elicit auditory evoked potentials.

16. The device of claim 1, wherein the base unit is configured to transmit data to another mobile or stationary device to facilitate more complex data processing or analysis.

17. The device of claim 1, wherein the base unit comprises a display screen to display a result of the multimodal assessment of the subject's neurological condition.

18. The device of claim 1, wherein the base unit comprises a wireless transceiver to transmit a result of the multimodal assessment wirelessly to a remote network, computer, or to an external memory device to store the result.

* * * * *